United States Patent
Schmidhammer

[11] Patent Number: 5,886,001
[45] Date of Patent: Mar. 23, 1999

[54] AGONIST COMPOUNDS

[75] Inventor: Helmut Schmidhammer, Innsbruck, Austria

[73] Assignee: Astra AB, Sweden

[21] Appl. No.: 507,365

[22] PCT Filed: May 9, 1995

[86] PCT No.: PCT/SE95/00504

§ 371 Date: Aug. 22, 1995

§ 102(e) Date: Aug. 22, 1995

[87] PCT Pub. No.: WO95/31464

PCT Pub. Date: Nov. 23, 1995

[30] Foreign Application Priority Data

May 18, 1994 [SE] Sweden .................................. 9401727

[51] Int. Cl.[6] .............................................. A61K 31/445
[52] U.S. Cl. .............................. 514/279; 546/35; 546/44; 546/45
[58] Field of Search .............................. 514/279; 546/35, 546/37

[56] References Cited

U.S. PATENT DOCUMENTS

| | | | |
|---|---|---|---|
| 4,816,586 | 3/1989 | Portoghese | 544/340 |
| 5,223,507 | 6/1993 | Dappen et al. | 514/279 |
| 5,225,417 | 7/1993 | Dappen et al. | 514/279 |
| 5,332,818 | 7/1994 | Nagase et al. | 546/37 |
| 5,631,263 | 5/1997 | Portoghese | 546/37 |
| 5,780,479 | 7/1998 | Kim | 514/279 |

FOREIGN PATENT DOCUMENTS

| | | |
|---|---|---|
| 0577847 | 1/1994 | European Pat. Off. |
| 614898 | 9/1994 | European Pat. Off. |
| 94-07896 | 4/1994 | WIPO . |

OTHER PUBLICATIONS

Burks et al., "Regulation of Gastrointestinal Function by Multiple Opioid Receptors," *Life Sci.* 43:2177–2181 (1988).
Frederickson et al., "Metkephamid, a Systemically Active Analog of Methionine Enkephalin with Potent Opioid δ–Receptor Activity," *Science* 211:603–605 (1981).
Krames et al., "Intrathecal D–Ala$^2$–D–Leu$^5$–enkephalin (DADL) Restores Analgesia in a Patient Analgetically Tolerant to Intrathecal Morphine Sulfate," *Pain* 24:205–209 (1986).

*Primary Examiner*—Donald G. Daus
*Attorney, Agent, or Firm*—Michael A. Sanzo; Vinson & Elkins L.L.P.

[57] ABSTRACT

New morphinane derivatives of the formula (I)

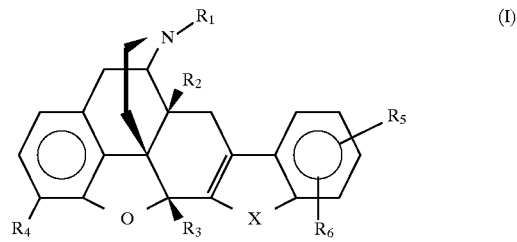

their pharmaceutically acceptable salts, a process for their preparation and their use in therapy. The variables in the above structure are as follows: $R_1$ is selected from the group consisting of $C_1$–$C_6$ alkyl and hydrogen;

$R_2$ is selected from the group consisting of hydrogen; hydroxy; $C_1$–$C_6$ alkoxy; $C_7$–$C_{16}$ arylalkyloxy, wherein the aryl is $C_6$–$C_{10}$ aryl and the alkyloxy is $C_1$–$C_6$ alkyloxy;

$R_3$ is a $C_1$–$C_6$ alkyl;

$R_4$ is a hydrogen; hydroxy; or a $C_1$–$C_6$ alkoxy;

$R_5$ and $R_6$ each and independently are selected from the group consisting of hydrogen; and $C_1$–$C_6$ alkyl;

X is $NR_9$, wherein $R_9$ is selected from the group consisting of hydrogen; and $C_1$–$C_6$ alkyl;

and wherein any aryl group in the compound may be unsubstituted or mono-, di-, or tri-substituted independently with hydroxy; halo; nitro; cyano; thiocyanato; trifluoromethyl; $C_1$–$C_3$ alkyl; $C_1$–$C_3$ alkoxy; $CO_2H$; $CONH_2$; $CO_2(C_1$–$C_3$ alkyl); $CONH(C_1$–$C_3$ alkyl); $CON(C_1$–$C_3$ alkyl)$_2$; $CO(C_1$–$C_3$ alkyl); amino; ($C_1$–$C_3$ monoalkyl) amino; ($C_1$–$C_3$ dialkyl) amino; $C_5$–$C_6$ cycloalkylamino; ($C_1$–$C_3$ alkanoyl) amido; SH; $SO_3H$; $SO_3(C_1$–$C_3$ alkyl); $SO_2(C_1$–$C_3$ alkyl); $SO(C_1$–$C_3$ alkyl); $C_1$–$C_3$ alkylthio; and $C_1$–$C_3$ alkanoylthio.

9 Claims, No Drawings

AGONIST COMPOUNDS

FIELD OF THE INVENTION

The present invention is related to novel δ opioid receptor agonists as well as to their pharmaceutically acceptable salts, a process for their preparation and their use in the manufacture of pharmaceutical preparations.

BACKGROUND OF THE INVENTION

Three major types of opioid receptors, μ, κ and δ, are known and characterized. The identification of different opioid receptors has lead to efforts to develop specific ligands for these receptors. These ligands are known to be useful for at least two purposes:

a) to enable the more complete characterization of these different receptors, and b) to facilitate the identification of new analgesic drugs.

Analgesic drugs having specificity for an individual opioid receptor type have been demonstrated to have fewer side effects (e.g. respiratory depression, constipation, dependence), and in cases in which tolerance to one drug has developed, a second drug with different opioid receptor specificity may be effective. For example the successful substitution of DADLE (intrathecal application), a partially δ-selective analgesic peptide, for morphine in a human cancer patient with morphine tolerance has been demonstrated (E. S. Krames et al., Pain, Vol. 24:205–209, 1986). Evidence that a δ-selective agonist could be a potent analgesic with less tolerance and dependence liability was presented by Frederickson et al. (Science, Vol. 211:603–605, 1981). The peptide, [D-Ala$^2$,N-MeMet$^5$]enkephalin amide or "metkephanuid", was hundred fold more potent than morphine in the hot-plate test for analgesia after i. c. v. (intracerebral ventricular) administration. Naloxone precipitation of withdrawal after chronic administration of metkephamid and morphine in rats showed that metkephamid-treated animals exhibited fewer withdrawal symptoms than those given morphine, scoring only a little above the saline control group. Meltkephamid produced substantially less respiratory depression than morphine.

Another δ-selective peptide, [D-Pen$^2$, D-Pen$^5$]enkephalin (DPDPE) produces potent analgesic effects while showing little if any respiratory depression (C. N. May, Br.J. Pharmacol., Vol.98:903–913, 1989). DPDPE was found not to produce gastrointestinal side effects (e.g. constipation) (T. F.Burks, Life Sci., Vol.43:2177–2181, 1988). Since it is desireable that analgesics are stable against peptidases and are capable of entering the CNS easily, non-peptide analgesics are much more valuable.

PRIOR ART

Recently a non-peptide, δ-selective opioid agonist, BW373U86—a piperazine derivative, has been disclosed. BW 373U86 is reported to be a potent analgesic which does not produce physical dependence (P. H. K. Lee et al., J.Pharmacol.Exp.Ther., Vol. 267:983–987, 1993).

An undesired side effect of this compound is that it produces convulsions in animals. The convulsions were antagonized by the δ-selective opioid antagonist naltrindole.

OUTLINE OF THE INVENTION

The present invention provides novel analgesic compounds of the formula I

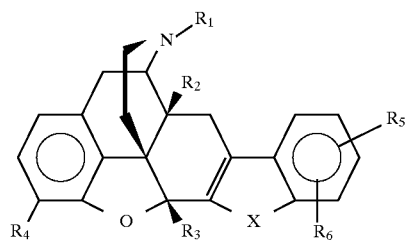

wherein $R_1$ represents $C_1$–$C_6$ alkyl or hydrogen;

$R_2$ represents hydrogen, hydroxy, $C_1$–$C_6$, alkoxy; $C_1$–$C_6$ alkenyloxy; $C_7$–$C_{16}$ arylalkyloxy wherein the aryl is $C_6$–$C_{10}$ aryl and the alkyloxy is $C_1$–$C_6$ alkyloxy; $C_7$–$C_{16}$ arylalkenyloxy wherein the aryl is $C_6$–$C_{10}$ aryl and the alkenyloxy is $C_1$–$C_6$ alkenyloxy; $C_1$–$C_6$ alkanoxyloxy, $C_1$–$C_6$ alkenoyloxy, $C_7$–$C_{16}$ arylalkanoyloxy wherein the aryl is $C_6$–$C_{10}$ aryl, and the alkanoyloxy is $C_1$–$C_6$ alkanoyloxy;

$R_3$ represents hydrogen, $C_6$–$C_6$ alkyl; $C_1$–$C_6$ alkenyl; $C_7$–$C_{16}$ arylalkyl wherein the aryl is $C_6$–$C_{10}$ aryl and the alkyl is $C_1$–$C_6$ alkyl; $C_7$–$C_{16}$ arylalkenyl wherein the aryl is $C_6$–$C_{10}$ aryl and the alkenyl is $C_1$–$C_6$ alkenyl; hydroxy($C_1$–$C_6$)alkyl; alkoxyalkyl wherein the alkoxy is $C_1$–$C_6$ alkoxy and the alkyl is $C_1$–$C_6$ alkyl; $CO_2H$; $CO_2(C_1$–$C_6$ alkyl);

$R_4$ is hydrogen, hydroxy; $C_1$–$C_6$ alkoxy; $C_7$–$C_{16}$ arylalkyloxy wherein the aryl is $C_6$–$C_{10}$ aryl and the alkyloxy is $C_1$–$C_6$ akyloxy; $C_1$–$C_6$ alkenyloxy; $C_1$–$C_6$ alkanoyloxy; $C_7$–$C_{16}$ arylalkanoyloxy wherein the aryl is $C_6$–$C_{10}$ aryl and the alkanoyloxy is $C_1$–$C_6$ alkanoyloxy; alkyloxyalkoxy wherein alkyloxy is $C_1$–$C_4$ alkyloxy and alkoxy is $C_1$–$C_6$ alkoxy;

$R_5$ and $R_6$ each independently represent hydrogen; OH; $C_1$–$C_6$ alkoxy; $C_1$–$C_6$ alkyl; hydroxyalkyl wherein the alkyl is $C_1$–$C_6$ alkyl; halo; nitro; cyano; thiocyanato; trifluoromethyl; $CO_2H$; $CO_2(C_1$–$C_6$ alkyl); $CONH_2$; CONH ($C_1$–$C_6$ alkyl); CON($C_1$–$C_6$ alkyl)$_2$; amino; $C_1$–$C_6$ monoalkyl amino; $C_1$–$C_6$ dialkyl amino; $C_5$–$C_6$ cycloalkylamnino; SH; $SO_3H$; $SO_3(C_1$–$C_6$ alkyl); $SO_2$ ($C_1$–$C_6$ alkyl); $SO_2NH_2$; $SO_2NH(C_1$–$C_6$ alkyl); $SO_2NH(C_7$–$C_{16}$ aryalkyl); $SO(C_1$–$C_6$ alkyl); or $R_5$ and $R_6$ together form a phenyl ring which may be unsubstituted or substituted by halo, nitro, cyano, thiocyanato; $C_1$–$C_6$ alkyl; trifluoromethyl; $C_1$–$C_6$ alkoxy, $CO_2H$, $CO(C_1$–$C_6$ alkyl), amino, $C_1$–$C_6$ monoalkylamino, $C_1$–$C_6$ dialkylamino, SH; $SO_3H$; $SO_3(_1$–$C_6$ alkyl), $SO_2(C_1$–$C_6$ alkyl), $SO(C_1$–$C_6$ alkyl), and X represents oxygen; sulfur; CH═CH; or $NR_9$ wherein $R_9$ is H, $C_1$–$C_6$ alkyl, $C_1$–$C_6$ alkenyl; $C_7$–$C_{16}$ arylalkyl wherein the aryl is $C_6$–$C_{10}$ aryl and the alkyl is $C_1$–$C_6$ alkyl, $C_7$–$C_{16}$ arylalkenyl wherein the aryl is $C_6$–$C_{10}$ aryl and the alkenyl is $C_1$–$C_6$ alkenyl; $C_1$–$C_6$ alkanoyl, and wherein aryl is unsubstituted or mono-, di- or trisubstituted independently with hydroxy, halo, nitro, cyano, thiocyanato, trifluoromethyl, $C_1$–$C_3$ alkyl, $C_1$–$C_3$ alkoxy, $CO_2H$, $CONH_2$ $CO_2(C_1$–$C_3$ alkyl), CONH ($C_1$–$C_3$ alkyl), CON($C_1$–$C_3$ alkyl)$_2$ $CO(C_1$–$C_3$ alkyl); amino; ($C_1$–$C_3$ monoalkyl)amino, ($C_1$–$C_3$ dialkyl)amino, $C_5$–$C_6$ cycloalkylamino, ($C_1$–$C_3$ alkanoyl) amido, SH, $SO_3H$, $SO_3(C_1$–$C_3$ alkyl), $SO_2(C_1$–$C_3$ alkyl), $SO(C_1$–$C_3$ alkyl), $C_1$–$C_3$ alkylthio or $C_1$–$C_3$ alkanoylthio;

and the pharmacologically acceptable salts of the compounds of the formula (I).

Aryl may be unsubstituted or mono-, di- or trisubstituted independently with hydroxy, halo, nitro, cyano, thiocyanato, trifluoromethyl, $C_1$–$C_3$ alkyl, $C_1$–$C_3$ alkoxy, $CO_2H$, $CONH_2$, $CO_2(C_1$–$C_3$ alkyl), $CONH(C_1$–$C_3$ alkyl), $CON(C_1$–$C_3$ alkyl)$_2$, $CO(C_1$–$C_3$ alkyl); amino; ($C_1$–$C_3$ monoalkyl)amino, ($C_1$–$C_3$ dialkyl)amino, $C_5$–$C_6$ cycloalkylamino; ($C_1$–$C_3$ alkanoyl)amido, SH, $SO_3H$, $SO_3(C_1$–$C_3$ alkyl), $SO_2(C_1$–$C_3$ alkyl), $SO(C_1$–$C_3$ alkyl), $C_1$–$C_3$ alkylthio or $C_1$–$C_3$ alkanoylthio.

The above given definition for aryl is valid for all substituents in the present application where aryl is present.

Pharmaceutically and pharmacologically acceptable salts of the compounds of formula I include suitable inorganic salts and organic salts which can be used according to the invention. Examples of inorganic salts which can be used are HCl salt, HBr salt, sulfuric acid salt and phosphoric acid salt. Examples of organic salts which can be used according to the invention are methanesulfonic acid salt, salicylic acid salt, fumaric acid salt, maleic acid salt, succinic acid salt, aspartic acid salt, citric acid salt, oxalic acid salt and orotic acid salt. These examples are however not in any way limiting the salts which could be used according to the invention.

The novel δ-selective morphinane derivatives of the formula I are useful as analgesics without having dependence liability. They may be administered parenterally or non-parenterally. Specific routes of administration include oral, rectal, topical, nasal, ophthalmic, subcutaneous, intramuscular, intravenous, intrathecal, transdermal, intraarterial, bronchial, lymphatic and intrauterine administration. Formulations suitable for parenteral and oral administration are preferred.

In a preferred embodiment $R_1$ is selected from hydrogen, methyl, ethyl, n-propyl or isopropyl;

$R_2$ is selected from methoxy, ethoxy, n-propyloxy, benzyloxy, benzyloxy substituted in the aromatic ring with F, Cl, $NO_2$, CN, $CF_3$, $CH_3$, $OCH_3$, allyloxy, cinnamyloxy or 3-phenylpropoxy;

$R_3$ is selected from hydrogen, methyl, ethyl, benzyl or allyl;

$R_4$ is selected from hydroxy, methoxy, methoxymethoxy or acetyloxy;

$R_5$ and $R_6$ are each and independently selected from hydrogen, nitro, cyano, chloro, fluoro, bromo, trifluoromethyl, $CO_2H$, $CO_2CH_3$, $CONH_2$, $CONH CH_3$, SH, $SO_2NH_2$, $N(CH_3)_2$, $SO_2CH_3$ and X is selected from O, NH, $NCH_3$, N-benzyl, N-allyl.

In an especially preferred embodiment $R_1$ is $CH_3$;

$R_2$ is selected from methoxy, ethoxy, n-propyloxy, benzyloxy or benzyloxy substituted in the aromatic ring with chlorine $R_3$ is selected from hydrogen or $CH_3$;

$R_4$ is hydroxy;

$R_5$ and $R_6$ are each and independently selected from hydrogen, $CO_2H$, $CONH_2$, $SO_2NH_2$, or $SO_2CH_3$; and X is selected from O or NH.

The best mode known at present is to use the compound according to Example 1.

PREPARATION OF THE COMPOUNDS

The compounds represented by formula (I) wherein $R_3$ is $C_1$–$C_6$ alkyl, $C_7$–$C_{16}$ aralkyl wherein the aryl is $C_6$–$C_{10}$ aryl and the alkyl is $C_1$–$C_6$ alkyl; alkoxyalkyl wherein the alkoxy is $C_1$–$C_6$ alkoxy and the alkyl is $C_1$–$C_6$ alkyl; $CO_2(C_1$–$C_6$ alkyl); $C_1$–$C_6$alkanoyl; may be obtained by the following methods:

Thebaine of the formula

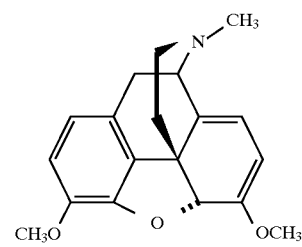

is being treated with dialkylsulfates, fluorosulfonic acid alkyl esters, alkylsulfonic acid alkyl esters, arylsulfonic acid alkylesters, alkyl halides, alkenyl halides, aralkyl halides, alkylsulfonic acid aralkyl esters, arylsulfonic acid aralkyl esters, arylalkenyl halides or chloroformates, in solvents such as tetrahydrofurane or diethyl ether using a strong base such as n-butyl lithium, lithium diethyl amide or lithium diisopropyl amide at low temperatures (−20° to −80° C.) (s. Boden et al., J.Org.Chem., Vol.47:1347–1349, 1982, Schmidhammer et al., Helv.Chim. Acta. Vol.71:642–647, 1988, Gates et al., J.Org. Chem. Vol. 54; 972–974, 1984), giving compounds of formula (II),

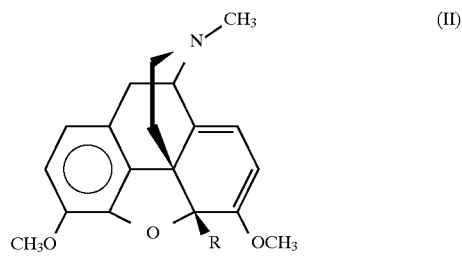

wherein R is $C_1$–$C_6$ alkyl; $C_1$–$C_6$ alkenyl; $C_7$–$C_{16}$ arylalkyl, wherein the aryl is $C_6$–$C_{10}$ aryl and the alkyl is $C_1$–$C_6$ alkyl; $C_7$–$C_{16}$ arylalkenyl wherein the aryl is $C_6$–$C_{10}$ aryl and the alkenyl is $C_1$–$C_6$ alkenyl; alkoxyalkyl wherein the alkoxy is $C_1$–$C_6$ alkoxy and the alkyl is $C_1$–$C_6$ alkyl; $CO_2(C_1$–$C_6$ alkyl);

The 5-substituted thebaine derivatives (formula II) or thebaine are converted into the corresponding 14-hydroxycodeinones (compounds of formula III)

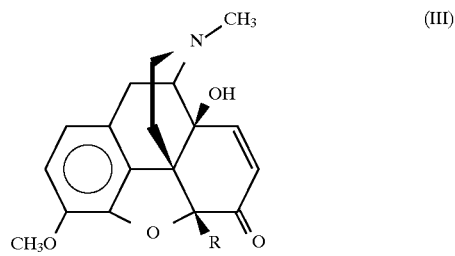

wherein R is as defined above or being hydrogen, by reaction with performic acid (H. Schmidhammer et al., Helv.Chim.Acta, Vol. 71:1801–1804, 1988) or m-chloroperbenzoic acid, at a temperature between 0° and 60° C. The preferred procedure is the reaction with performic acid at 0°–10 20° C. (H.Schmidhammer et.al., Helv. Chim. Acta. Vol. 71:1801–1804, 1988). These 14-hydroxycodeinones are being treated with dialkyl sulfates, alkyl halides, alkenyl halides, arylalkyl halides, arylalkenyl halides or chloroformates, in solvents such as N,N-dimethyl formamide or tetrahydrofurane using a strong base such as sodium hydride, potassium hydride or sodium amide giving compounds of formula (IV)

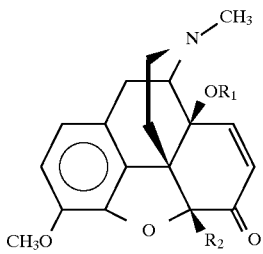 (IV)

wherein

R$_1$ is C$_1$–C$_6$ alkyl, C$_1$–C$_6$ alkenyl, C$_7$–C$_{16}$ arylalkyl wherein the aryl is C$_6$–C$_{10}$ aryl and the alkyl is C$_1$–C$_6$ alkyl, C$_7$–C$_{16}$ arylalkenyl wherein the aryl is C$_6$–C$_{10}$ aryl and the alkenyl is C$_1$–C$_6$ alkenyl, C$_1$–C$_6$ alkanoyl, C$_7$–C$_{16}$ arylalkanoyl wherein the aryl is C$_6$–C$_{10}$ aryl and the alkanoyl is C$_1$–C$_6$ alkanoyl, C$_7$–C$_{16}$ arylalkenoyl wherein the aryl is C$_6$–C$_{10}$ aryl and the alkenoyl is C$_1$–C$_6$ alkenoyl;

R$_2$ is hydrogen; C$_1$–C$_6$ alkyl; C$_1$–C$_6$ alkenyl C$_7$–C$_{16}$ arylalkyl wherein the aryl is C$_6$–C$_{10}$ aryl and the alkyl is C$_1$–C$_6$ alkyl; C$_7$–C$_{16}$ arylalkenyl wherein the aryl is C$_6$–C$_{10}$ aryl and the alkenyl is C$_1$–C$_6$ alkenyl; alkoxyalkyl wherein the alkoxy is C$_1$–C$_6$ alkoxy and the alkyl is C$_1$–C$_6$ alkyl; CO$_2$(C$_1$–C$_6$ alkyl);

which compounds in turn are reduced by catalytic hydrogenation using a catalyst such as palladium on charcoal and solvents such as methanol, ethanol, or glacial acetic acid to give compounds of formula (V)

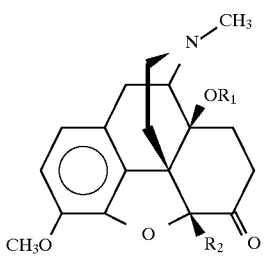 (V)

wherein

R$_1$ is C$_1$–C$_6$ alkyl, C$_7$–C$_{16}$ arylalkyl wherein the aryl is C$_6$–C$_{10}$ aryl and the alkyl is C$_1$–C$_6$ alkyl, C$_1$–C$_6$ alkanoyl, C$_7$–C$_{16}$ arylalkanoyl wherein the aryl is C$_6$–C$_{10}$ aryl and the alkanoyl is C$_1$–C$_6$ alkanoyl;

R$_2$ is hydrogen; C$_1$–C$_6$ alkyl, C$_7$–C$_{16}$ arylalkyl wherein the aryl is C$_6$–C$_{10}$ aryl and the alkyl is C$_1$–C$_6$ alkyl; alkoxyalkyl wherein the alkoxy is C$_1$–C$_6$ alkoxy and the alkyl is C$_1$–C$_6$ alkyl; CO$_2$(C$_1$–C$_6$ alkyl);

Ether cleavage of these compounds using boron tribromide (in a solvent such as dichloro methane or chloroform) at about 0 20° C., 48% hydrobromic acid (reflux), or other well known reagents gives phenolic compounds of formula (VI),

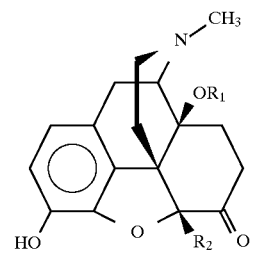 (VI)

wherein R$_1$ and R$_2$ are as defined above in formula (V).

Alkylation using alkyl halides, alkyl sulfates, sulfonic acid esters, aralkyl halides, arylalkenyl halides, or acylation using carbonic acid chlorides, carbonic acid anhydrides, or carbonic acid esters affords compounds of formula (VII)

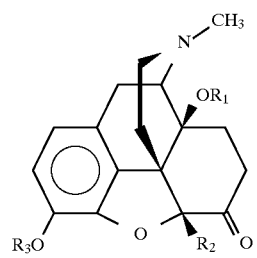 (VII)

wherein R$_1$ and R$_2$ are as definded above in formula (V), and

R$_3$ is C$_1$–C$_6$ alkyl, C$_7$–C$_{16}$ arylalkyl wherein the aryl is C$_6$–C$_{10}$ aryl and the alkyl is C$_1$–C$_6$ alkyl, C$_1$–C$_6$ alkenyl, C$_7$–C$_{16}$ arylalkanoyl wherein the aryl is C$_6$–C$_{10}$ aryl and the alkanoyl is C$_1$–C$_6$ alkanoyl, alkyloxyalkyl wherein alkyloxy is C$_1$–C$_4$ alkyloxy and alkyl is C$_1$–C$_6$ alkyl, which after N-demethylation using for instance chloroformates or cyanogen bromide followed by cleavage of the corresponding carbamates or N-cyano compounds (compounds of formula VIII)

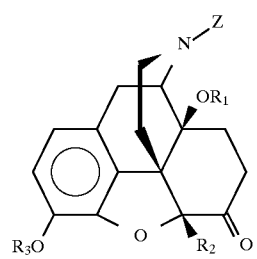 (VIII)

wherein R$_1$, R$_2$ and R$_3$ are as defined above in formula (V) and (VII), and Z is for instance CO$_2$CH=CH$_2$, CO$_2$CHClCH$_3$, CO$_2$CH$_2$CH$_3$, CO$_2$Ph, CO$_2$CH$_2$CCl$_3$ or CN by treatment with the adequate reagent such as aqueous acid, alkali, hydrazine, zinc, alcohol or the like N-nor derivatives of formula (IX)

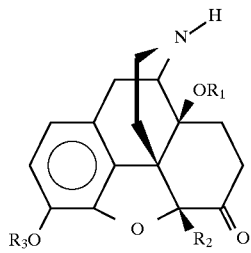

(IX)

wherein $R_1$, $R_2$ and $R_3$ are as defined above in formula (V) and (VII).

N-alkylation can be accomplished with alkyl halide or dialkyl sulfate in solvents such as dichloro methane, chloroform or N,N-dimethyl formamide in the presence of a base such as sodium hydrogen carbonate or potassium carbonate to yield derivatives of formula (X)

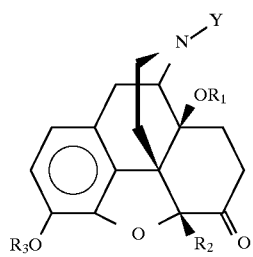

(X)

wherein $R_1$, $R_2$ and $R_3$ are as defined above in formula (V) and (VII), and Y is methyl, ethyl, n-propyl, n-butyl, n-pentyl, n-hexyl, isopropyl, isobutyl, tert-butyl, 2-pentyl, 3-pentyl, 2-hexyl or 3-hexyl.

Ether cleavage can be carried out as described for compounds of formula (V) giving derivatives of formula (XI)

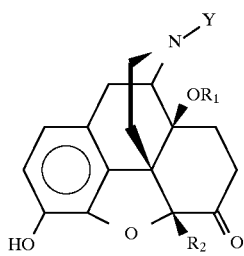

(XI)

wherein $R_1$ and $R_2$ are as defined above in formula (V), and Y is as defined above in formula (X).

Compounds according to formula (I) wherein $R_2$ is hydroxy may be obtained from compounds of the formula (III) wherein R is defined as above. These compounds can be reduced by catalytic hydrogenation using a catalyst such as palladium on charcoal and solvents such as methanol, ethanol, or glacial acetic acid to give compounds of formula (V) wherein $R_1$ is hydrogen and $R_2$ is as defined above.

The following reaction sequence and procedures leading to compounds of formula (VI), (VII), (VIII), (IX), (X), and (XI) wherein $R_1$ is hydrogen and wherein $R_2$ and $R_3$ are as defined above in formula (V) and (VII), is analogous to the reaction sequence and procedures described above. Further conversion into compounds of the formula (I) wherein $R_2$ is hydroxy is described below.

Compounds of the formula (I) wherein $R_2$ is hydrogen may be obtained from compounds of the formula (II) wherein R is as defined above. Catalytic hydrogenation followed by acid hydrolysis (s. Boden et al., J. Org. Chem. Vol. 47:1347–1349, 1982) gives compounds of the formula (XII)

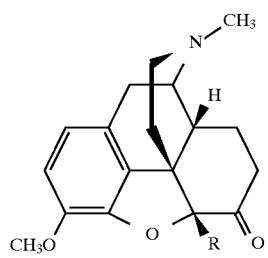

(XII)

(XII a):R = H (dihydrocodeinone)

wherein R is as defined above in formula (II).

Compounds of the formula (XII) and (XII a) (Mannich and Löwenheim, Arch. Pharm., Vol. 258:295, 1920) can be converted into compounds of the formula (V), (VI), (VII), (VIII), (IX), (X) and (XI) wherein the substitutent in position 14 is hydrogen and $R_2$ and $R_3$ are as defined above in formula (V) and (VII), similary as described above. Further conversion into compounds of the formula (I) wherein $R_2$ is hydrogen is described below.

Compounds of the formula (I) wherein $R_4$ is hydrogen may be prepared from compounds of the formulas (VI) or (XI) by alkylation with 5-chloro-1-phenyl-1H-tetrazole to give the corresponding phenyltetrazolyl ethers of the formula (XIV)

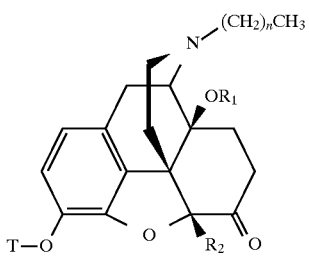

(XIV)

wherein $R_1$ and $R_2$ are defined as above, n is 0–5 and T is phenyltetrazolyl.

Catalytic hydrogenation may afford (H. Schmidhammer et al., J. Med. Chem. Vol. 27:1575–1579, 1984), compounds of the formula (XV)

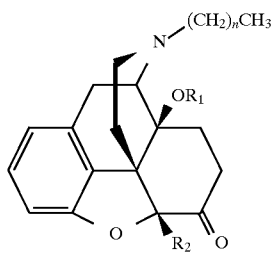

(XV)

wherein $R_1$ and $R_2$ are as defined above and n is 0–5.

Compounds according to the formula (I) wherein $R_2$ is as defined above and X represents NH are obtained by reaction of compounds of formula (VI), (VII), (IX), (X), (XI) or (XV) with phenylhydrazine or substituted phenylhydrazine in solvents such as methanol, ethanol or glacial acetic acid in the presence of methanesulfonic acid, HCl or HBr. Phenylhydrazine substituted at the aromatic ring with halogen, hydroxy, $C_1$–$C_6$ alkyl, $C_1$–$C_6$ alkoxy, amino, nitro, cyano, thiocyanato, trifluoromethyl, $CO_2H$, $CO_2(C_1$–$C_{16}$ alkyl), $CONH_2$, $CONH(C_1$–$C_6$ alkyl), $CON(C_1$–$C_6$ alkyl)$_2$, $SO_2NH_2$, $SO_2(C_1$–$_6$ alkyl) or the like may be employed. The reaction may be carried out at a temperature between 20° and 160 20° C., preferably between 20° and 80° C.

Compounds of formula (I) wherein $R_3$ is as defined above and X represents oxygen are obtained by reaction of compounds of formula (VI), (VII), (IX), (X), (XI) or (XV) with O-phenylhydroxylamine or substituted (at the aromatic ring) O-phenylhydroxylamine in solvents such as methanol, ethanol, or glacial acetic acid in the presence of methanesulfonic acid, HCl or HBr. O-Phenylhydroxylamine substituted at the aromatic ring with halogen, $C_1$–$C_6$ alkyl, amino, nitro, cyano, thiocyanato, trifluoromethyl, $CO_2H$, $CO_2$ ($C_1$–$C_6$ alkyl), $CONH_2$, $CONH(C_1$–$C_6$ alkyl), $CON(C_1$–$C_6$ alkyl$)_2SO_2NH_2,SO_2(C_1$–$C_6$ alkyl) or the like may be employed.

The following examples describe in detail the preparation of the compounds according to the invention.

EXAMPLE 1

Synthesis of 6,7-Dehydro-4,5α-epoxy-14-ethoxy-3-hydroxy-5,17-dimethyl-6,7-2',3'-indolomorphinan (compound 1).

A mixture of 14-ethoxymetopon (H. Schmidhammer et al. Helv. Chim Acta. Vol. 73:1784–1787, 1990) (500 mg, 1.45 mmol), phenylhydrazaine hydrochloride (340 mg, 2.35 mmol) and 10 ml of glacial acetic acid was refluxed for 48 h. After cooling, the reaction fixture was poured on ice, alkalized with conc. $NH_4OH$ and extracted with $CH_2Cl_2$ (3×10 ml). The combined organic layers were washed with. $H_2O$ (3×15 ml), dried over $Na_2SO_4$ and evaporated. The resulting residue (546 mg orange-brown foam) was crystallized with MeOH to yield 322 mg of the title compound which was further purified by column chromatography (alumina basic grade IV, elution with a) $CH_2Cl_2$, b) $CH_2Cl_2$/MeOH 99:1). After evaporation of the corresponding fractions, 237 mg of slightly yellow crystals were obtained. Recrystallization from MeOH yielded 116 mg (24%) of pure title compound 1. M.p. 165°–167° C. IR (KBr): 3285 (NH, OH)cm$^{-1}$. CI-MS:m/z 417 (M$^+$+1). $^1$H-NMR(CDCl$_3$): δ 8.15 (s, NH, OH), 7.35 (d, J=8 Hz, 1 arom. H), 7.26 (d, J=8 Hz, 1 arom. H), 7.13 (t, J=8 Hz, 1 arom. H), 7.01 (t, J=8 Hz, 1 arom. H), 6.64 (d, J=8 Hz, 1 arom. H), 6.55 (d. J=8 Hz, 1 arom. H), 2.40 (s, CH$_3$N), 1.94 (s, CH$_3$—C(5)), 1.02 (t. J=7 Hz, 3H, CH$_3$CH$_2$O). Analysis calculated for $C_{26}H_{28}N_2O_3$. (480.60): 69.98, H 7.55, N 5.83; found: C 70.23, H 7.40, N 5.87.

EXAMPLE 2

Synthesis of 6,7-Dehydro-4,5α-epoxy-3,14-dimethoxy-5,17-dimethyl-6,7-2',3'-indolomorphinan (compound 2).

A mixture of 5,14-O-dimethyloxycodone (H. Schmidhammer et al., Helv. Chim. Acta Vol. 73: 1784–1787, 1990) (300 mg, 0.87 mmol), phenylhydrazine hydrochloride (189 mg, 1.31 mmol), methanesulfonic acid (84 mg, 0.87 mmol), and 12 ml of glacial acetic acid was refluxed for 17 h. After cooling, the reaction mixture was poured on ice, alkalized with conc. $NH_4OH$ and extracted with $CH_2Cl_2$ (3×10 ml). The combined organic layers were washed with $H_2O$ (3×10 ml), dried over $Na_2SO_4$ and evaporated. The resulting residue (380 mg yellowish crystals) was recrystallized from MeOH to yield 336 mg (93%) of pure title compound 2 as slightly yellow crystals. M.p. 218°–221° C. (KBr): 3800 (NH) cm$^{-1}$. CI-MS: m/z 417 (M$^+$+1). $^1$H-NMR (CDCl$_3$): δ 8.30 (s, NH), 7.48 (d, J=8 Hz, 1 arom. H), 7.39 (d, J=8 Hz, 1 arom. H), 7.12 (t, J=8 Hz, 1 arom. H), 7.03 (t, J=8 Hz, 1 arom, H), 6.58 (s, 2 arom. H), 3.73 (s, OCH$_3$—C(3)), 3.28 (s, OCH$_3$—C(14)), 2.45 (s, NCH$_3$), 1.87 (s, CH$_3$—C(5)). Analysis calculated for $C_{26}H_{28}N_2O_3$. 2 MeOH (480.60): C 69.98, H 7.55, N5.83; found C 70.19, H 7.41, N 5.95.

EXAMPLE 3

Synthesis of 6,7-Dehydro-4,5α-epoxy-3-hydroxy-14-methoxy-5,17-dimethyl-6,7-2'3'-indolomorphinan (compound 3).

A mixture of 14-methoxymetopon hydrobromide (H. Schmidhammer et al., Helv. Chim. Acta Vol. 73: 1784–1787, 1900) (500 mg, 1.22 mmol) phenylhydrazine hydrochloride (211 mg, 1.46 inmol), and 10 ml of glacial acetic acid was refluxed for 24 h. After cooling, the reaction mixture was poured on ice, alkalized with conc. $NH_4OH$ and extracted with $CH_2Cl_2$ (3×10 ml). The combined organic layers were washed with $H_2O$ (3×15 ml), dried over $Na_2SO_4$ and evaporated. The resulting residue (455 mg slightly grey foam) was crystallized from MeOH to give 330 mg (67%) of pure title compound 3. M. p. 273°–276° C. (dec.). IR (KBr): 3300 (NH, OH) cm$^{-1}$. CI-MS: M/Z 403 (M$^+$+1). $^1$H-NMR (DMSO-d$_6$): δ 11.10 and 8.78 (2 s, NH, OH), 7.32 (dxd, J=8 HZ, 2 arom. H.) 7.07 (t, J=8 HZ, 1 arom. H), 6.91 (t, J=8 HZ, 1 arom. H), 6.44 (s, 2 arom. H), 3.32 (s. OCH$_3$), 2.33 (s, NCH$_3$), 1.81 (s, CH$_3$—C(5)). Analysis calculated for $C_{25}H_{26}N_2O_3$. 2 MeOH (466.56):C 69.50, H 7.35, N 6.01; found: C 69.78, H 7.38, N 6.09.

EXAMPLE 4

Synthesis of 6,7-Dehydro-4,5α-epoxy-3,14-dihydroxy-5,17-dimethyl-6,7-2'3'-indolomorphinan Hydrobromide (compound 4).

A mixture of 14-hydroxymetopon hydrobromide (H.Schmidhammer et al., Helv. Chim. Acta Vol. 71: 1801–1804, 1988) (450 mg, 0.95 mmol), phenylhydrazine hydrochloride (280 mg, 1.93 mmol), and 15 ml of glacial acetic acid was refluxed for 20 h. After cooling, the reaction mixture was poured on ice, alkalized with conc. $NH_4OH$ and extracted with $CH_2Cl_2$ (3×60 ml). The combined organic layers were washed with $H_2O$ (3×60 ml) and brine, dried over $Na_2SO_4$ and evaporated. The resulting residue (392 mg of a brownish foam) was dissolved in glacial acetic acid and treated with 48% HBr. The crystals were collected and recrystallized from glacial acetic acid to yield 132 mg (25%) of the title compound 4 as colorless crystals. M.p. >250° C. (dec.). IR (KBr)3300 ($^+$NH, OH)cm$^{-1}$. CI-MS:m/z 389(M$^+$ +1). $^1$H-NMR (DMSO-d$_6$): δ 11.28 (s, NH), 9.19 (s, OH—C (3)), 9.09 (broad s, $^+$NH), 7.10 (m, 4 arom. H), 6.56 (s, 2 arom. H)6.12(s, OH—C(14)), 2.88 (s, NCH$_3$), 1.88 (s, CH$_3$—C(5)). Analysis calculated for $C_{24}H_{24}N_2O_3$×HBr×0.1 $H_2O$ (489.20); C 58.93, H 5.60, N 5.73, Br 16.33; Found: C 59.01, H 5.55, N 5.56, Br 16.17.

EXAMPLE 5

Synthesis of 7,8-Dehydro-4,5a-epoxy-14-hydroxy-3-methoxy-5,17-dimethyl-6,7-2'3'-indolomorphinan Hydrobromide (compound 5).

A mixture of 5-methyloxycodon (H.Schmidhammer et al., Helv. Chim. Acta, Vol. 71: 1801–1804, 1988) (350 mg, 0.72 mmol), phenylhydrazine hydrochloride (260 mg, 1.79 mmol), and 15 ml of glacial acetic acid was refluxed for 18 h. After cooling, the reaction mixture was poured on ice, alkalized with conc. $NH_4OH$ and extracted with $CH_2Cl_2$ (3×50 ml). The combined organic layers were washed with H₂O (3×60 ml) and brine, dried over Na₂SO₄ and evaporated. The resulting residue (365 mg brownish foam) was dissolved in glacial acetic acid and treated with 48% HBr. The crystals were collected and recrystallized from glacial acetic acid to give 130 mg (25%) of pure title compound 5. HBr. M.p. >260° C. (dec.). IR (KBr): 3406, 3396, 3242 (NH, ⁺NH, OH)cm⁻¹. CI-MS: m/z 403(M⁺+1) ¹H-NMR (DMSO-d₆): δ 11.34 (s, NH), 9.20 (broad s ⁺NH), 7.05 (m, 4 arom. H), 6.76 (d, J=8,3 Hz, 1 arom. H). 6.69 (d, J=8.3 HZ, 1 arom. H), 6.17 (s, OH—C(14)), 3.65 (s, OCH₃), 2.90(s, NCH₃) 1.89 (s, CH₃—C(5)). Analysis calculated for $C_{25}H_{26}N_2O_3 \times$ HBr×0.9H₂O (499.63): C 60.10, H 5.81, N 5.61, Br 15.99; Found: C 60.11, H 5.97, N 5.55, Br 16.02.

EXAMPLE 6

Synthesis of 6,7-Dehydro-4,5α-epoxy-3-hydroxy-14-methoxy-5-methyl-6,7-2',3'-indolomorphinan (compound 7).

A solution of 4,5α-epoxy-3,14-dimethoxy-5-methylmorphinan-6-one hydrochloride (H. Schlnidhammer et al., Helv. Chim. Acta Vol. 77: 1585–1589, 1994) (1.0 g, 2.73 mmol) in 3.5 ml of 48% HBr was refluxed for 15 min. After cooling, the now brown solution was evaporated, the residue treated with MeOH and again evaporated (this operation was repeated once). The oily residue was crystallized from MeOH to yield 713 mg (66%) of colorless 4,5a-epoxy-3-hydroxy-14-methoxy-5-methylmorphinan-6-one hydrobromide (compound 6). M.p.>230° C. (dec.). IR (KBr): 3545 and 3495 (⁺NH, OH), 1720 (CO)cm⁻¹. CI-MS:m/z 316(M⁺+1). ¹H-NMR(DMSO-d₆):δ9.37 (s, OH), 8.65 (broad s, ⁺NH₂), 6.64 (dd, J=8.2, 8.2 Hz, 2 arom. H), 3.36 (s, OCH₃—C(14)), 1.48 (s, CH₃—C(5)). Analysis calculated for $C_{18}H_{21}NO_4$. HBr. MeOH(428.33):C 53.28, H 6.12, N 3.27; found: C 53.12, H 5.97, N 3.32.

A mixture of 4,5α-epoxy-3-hydroxy-14-methoxy-5-methylmorphinan-6-one hydrobromide (compound 6, 1.2 g, 3.03 mmol), phenylhydrazine hydrochloride (548 mg, 3.79 mmol), and 15 ml of glacial acetic acid was refluxed for 4 h. After cooling, the reaction mixture was evaporated to give a brownish solid (2.14 g) which was refluxed in 10 ml of MeOH for 5 min and the refrigerated. The solid was isolated (the mother liquor of this isolation was further processed, see below), dissolved in H₂O and alkalized with conc. NH₄OH. The precipitation was isolated to yield 569 mg (70%) of pure title compound 7. M.p.>270° C. (dec.). IR (KBr): 3395 and 3380 (NH, OH)cm⁻¹. EI-MS: m/z 388 (M⁺). Analysis calculated for $C_{24}H_{24}N_2O_3 \times 0.3$ H₂O (393.87): C 73.19, H 6.30, N 7.11; found: C 73.08, H 6.03, N 7.07.

Above mother liquor was evaporated and the resulting residue (566 mg) treated with 2 ml of hot MeOH to afford (after refrigeration) 201 mg (14%) of the title compound 7.HBr. M.p.>230° (dec.). ¹H-NMR of 7.HBr (DMSO-d₆): 11.30 (s, NH), 9.13 and 8.50 (2 s, ⁺NH, OH), 7.33 (dd, J=7.4, 7.4 Hz, 2 arom. H), 7.08 (t, J=7.4 Hz, 1 arom. H) 6.93(t, J=7.4 Hz, 1 arom. H), 6.57 (s, 2 arom. H), 3.32 (s, CH₃O—C(14)), 1.84 (s, CH₃—C(5)).

EXAMPLE 7

Synthesis of 6,7-Dehydro-4,5α-epoxy-3-hydroxy-5,17-dimethyl-14-n-propyloxy-6,7-2',3'-indolomorphinan methane sulfonate (compound 11)

A solution of 14-hydroxy-5-methylcodeinone (H. Schmidhammer et al., Helv. Chim. Acta Vol. 71: 1801–1804, 1988) (5.0 g, 15.27 mmol) in 50 ml of anhydrous N,N-dimethyl formamide was cooled to 0°–5° C. Sodium hydride (1.47 g, 15.27 mmol; obtained from 2,7 g of 60% sodium hydride dispersion in oil by washings with petroleum ether) was added under nitrogen atmosphere, and the resulting mixture stirred for 20 min. Then allyl bromide (2.64 ml, 30.54 mmol) was added in one portion, and stirring was continued at 0°–5° C. for 30 min. Excess sodium hydride was desroyed carefully with small pieces of ice, then the mixture was poured on 150 ml ice/H₂O. After extractions with CH₂Cl₂ (3×50 ml), the combined organic layers were washed with H₂O (3×100 ml) and brine, dried over Na₂SO₄ and evaporated to yield 6.43 g of a slightly yellow crystalline residue. Treatment with boiling ethanol (6 ml) gave (after refrigeration) 3.01 g (54%) of 14-allyloxy-5-methylcodeinone (compound 8). M.p. 136°–137° C. IR(KBr): 1664 (CO)cm⁻¹. CI-MS:m/z 368(M⁺+1). ¹H-NMR (DMSO-d₆): δ 6.78 (d, J=10.2 Hz, 1 olef.H.), 6.62 (d, J=8.2 Hz , 1 arom.H), 6.54 (d, J=8.2 Hz, 1 arom. H), 6.09 (d, J=10.2 Hz, 1 olef.H), 5.87 (m, 1 olef. H), 5.15 (m, 2 olef.H), 3.79 (s, CH₃O), 2.44 (s, CH₃N), 1.71 (s, CH₃—C (5)). Analysis calculated for $C_{22}H_{25}NO_4$(367.45): C 71.91, H 6.86, N 3.81; found: C 71.69, H 7.03, N 3.75.

A mixture of 14-allyloxy-5-methylcodeinone (compound 8;3,2 g, 10.64 mmol), 196 mg of 10% Pd/C catalyst, and 100 ml of ethanol was hydrogenated at 30 psi and room temperature for 3 h. The catalyst was filtered off and the filtrate evaporated. The residue (3.79 g colorless oil) was crystallized from ethanol to yield 2.93 g (74%) of 7,8-dihydro-5-methyl-14-n-propyloxycodeinone (compound 9). M.p. 102°–104° C. IR (KBr): 1718 (CO) cm⁻¹. CI-MS:m/z 372 (M⁺+1). ¹H-NMR (DMSO-d₆): δ 6.50 (dd, J=8,8 Hz, 2 arom. H), 4.76 (s, CH₃O), 2.35 (s, CH₃N), 1.61 (s, CH₃.C (5)), 1.00 (t, J=7 Hz, CH₃). Analysis calculated for $C_{22}H_{29}NO_4$. 0.2 EtOH (380.69): C 70.67, H 8.00, N 3.68; found: C 70.64, H 7.72, N 3.69. A 1M solution of boron tribornide in CH₂Cl₂ (54 ml) was added at once to an ice-cooled solution of 7,8-dihydro-5-methyl-14-n-propyloxycodeinone (compound 9; 2.7 g, 7.27 mmol) in 370 ml of CH₂Cl₂. After 2 h stirring at 0°–5° C., a mixture of 90 g of ice and 20 ml of conc. NH₄OH was added. The resulting mixture was stirred at room temperature for 30 min and then extracted with CH₂Cl₂ (3×200 ml). The combined organic layers were washed with brine (300 ml), dried over Na₂SO₄ and evaporated. The residue (2.4 g slightly brown foam) was crystallized from MeOH to give 1.48 g (57%) of 4,5α-epoxy-3-hydroxy-5,17-dimethyl-14-n-propyloxymorphinan-6-one (compound 10) as slightly brown crystals. An analytical sample was obtained by recrystallization of a small amount from MeOH. M.p. 193°–195° C. IR (KBr): 3376 (OH), 1726 (CO) cm⁻¹. EI-MS: m/z 357 (M⁺). ¹H-NMR (CDCl₃): δ 6.67 (d, J=8.1 Hz, 1 arom. H), 6.52 (d, J=8.1 Hz, 1 arom. H), 1.57 (s, CH₃—C(5)), 0.96 (t, J =7.2 Hz, CH₃). Analysis calculated for $C_{21}H_{27}NO_4$ (357.43): C 70.56, H 7.61, N 3.92; found: C 70.50, H 7.88, N 3.92.

A mixture of 4,5α-epoxy-3-hydroxy-5,17-dimethyl-14-n-propyloxymorphinan-6-one (compound 10; 350 mg, 0.97 mmol), phenylhydrazine hydrochloride 212 mg, 1.47 mmol), and 20 ml of glacial acetic acid was refluxed for 24 h. After cooling, the reaction mixture was poured on ice and alkalized with conc. NH₄OH and extracted with CH₂Cl₂ (3×40 ml). The combined organic layers were washed with H$_2$O (3×50 ml) and brine, dried over Na$_2$SO$_4$ and evaporated. The resulting residue (276 mg brown foam) was dissolved in MeOH and treated with methanesulfonic acid to give 180 mg of the title compound. Recrystallization from MeOH yielded 44 mg (9%) of pure compound 11. M. p. >270° C. IR (KBr): 3203 (NH) cm$^{-1}$. $^1$H-NMR (DMSO-d$_6$): δ 11.29 (s, NH), 9.13 (s, OH), 8.47 (broad s, $^+$NH), 7.15 (m, 4 arom. H), 6.58 (s, 2 arom. H), 2.97 (s. NCH$_3$), 1.86 (s, CH$_3$—C(5)), 0.57 (t, J=7.3 Hz, CH$_3$). Analysis calculated for C$_{27}$H$_{30}$N$_2$O$_3$. CH$_3$SO$_3$H. 0,7 H$_2$O (539.27): C 62.36, H 6.62, N 5.19, S 5.95; found: C 62.36, H 6.50, N 5.20, S 6.02.

EXAMPLE 8

Synthesis of 6,7-Dehydro-4,5α-epoxy-14-ethoxy-3-methoxy-17-methyl-6,7-2',3'-indolomorphinan. (Compound 12).

A mixture of 14-O-ethyloxycydone hydrochloride (R. J. Kobylecki et al, J. Med. Chem. Vol. 25: 116–120, 1982) (580 mg, 1.53 mmol), phenylhydrazine hydrochloride (265 mg, 1.83 mmol), and 8 ml of glacial acetic acid was stirred for five days at room temperature. The mixture was poured on ice, alkalized with conc. NH$_4$OH and extractred with CH$_2$Cl$_2$ (3×10 ml). The combined organic layers were washed with H$_2$O (3×15 ml), dried over Na$_2$SO$_4$ and evaporated. The resulting residue (590 mg slightly orange foam) was crystallized from MeOH to yield 360 mg (56%) of compound 12. M.p. 143°–145° C. (dec.) IR (Kbr): 3260 (NH)cm$^{-1}$. Cl-MS:m/z 417 (M$^+$+1). $^1$H-NMR(CDCl$_3$): δ 8.22 (s, NH, OH), 7.39 (d, J=8 Hz, 1 arom. H), 7.30 (d, J=8 Hz, 1 arom. H), 7.15 (t, J=8 Hz, 1 arom. H), 1 arom. H), 7.02 (t, J=8 Hz, 1 arom. H), 6.58 (s, 2 arom. H), 5.66 (s, H—C(5)), 3.74 (s, CH$_3$O), 2.39 (s, CH$_3$N), 1.01 (t, J=7 Hz, 3H, CH$_3$CH$_2$O). Analysis calculated for C$_{26}$H$_{28}$N$_2$O$_3$. 1.0 MeOH (448.56): C 72.30, H 7.19, N 6.25; found: C 72.50, H 6.93, N 6.58.

EXAMPLE 9

Synthesis of 6,7-Dehydro-4,5α-epoxy-14-ethoxy-17-isopropyl-3-methoxy-5-methyl-6,7-2',3'-benzo[b]furanomorphinan (compound 14).

A mixture of 14-ethoxy-7,8-dihydronorcodeinone hydrochloride (R. J. Kobylecki et al., J. Med. Chem., Vol. 25:116, 1982) (1.5 g, 4.1 mmol), potassium carbonate (3.2 g, 22.52 mmol), isopropyl bromide (1.2 ml, 13.31 mmol), and anhydrous N,N-dimethylformarnide (15 ml) was stirred at 50° C. (bath temperature) for 7 days. The inorganic solid was filtered off, the filtrate evaporated, dissolved in 40 ml of CH$_2$Cl$_2$ and washed with H$_2$O (3×30 ml). The organic phase was dried over Na$_2$SO$_4$ and evaporated to give 1.79 colorless crystals. Recrystallization from 1.7 ml of MeOH afforded 1.15 g (76%) of compound 13 (=14-ethoxy-17-isopropyl-7,8-dihydronorcodeinone). M.p. 188°–190° C. IR (Kbr): 1718 (CO) cm$^{-1}$. $^1$H NMR (CDCl$_3$): δ 6.65 (d, J=8.3 Hz, 1 arom. H), 6.56 (d, J =8.3 Hz, 1 arom H), 4.62 (s, H—C(5)), 3.87 (s, CH$_3$O), 1.23 (t, J=6.8 Hz, 3 H, CH$_3$CH$_2$O). Cl—MS (m7z 372 (M$^+$+1). Analysis calculated for C$_{22}$H$_{29}$NO$_4$×0.2 MeOH (377.89): C 70.56, H 7.95, N 3.71; found: C 70.43, H 7.64, N 3.70.

A mixture of compound 13 (250 mg, 0.67 rnmol), O-phenylhydroxylamnine hydrochloride (196 mg, 1.34 mmol), methanesulfonic acid (0.1 ml) and anhydrous methanol (6 ml) was refluxed for 6 days. After cooling, the solution was alkalized with conc. NH$_4$OH and extracted with CH$_2$Cl$_2$ (3×50 ml). The combined organic layers were washed with H$_2$O (3×50 ml) and brine (30 ml) and evaporated to give 217 mg of a brown foam which was crystallized from methanol to afford 102 mg of brownish crystal which were recrystallized from methanol to yield 33 mg (11%) of pure compound 14. M.p. 199°–201° C. $^1$H NMR (CDCl$_3$): δ 7.10–6.42 (m, 6 arom. H), 4.90 (s, H—C(5)), 3.98 (s, 3 H, CH$_3$O), 1.29 (t, J=6.7 Hz, 3 H, CH$_3$CH$_2$O), 1.08 (dd, J=6.1 Hz, 2 CH$_3$). CI-MS: m/z 446 (M$^+$+1). Analysis calculated for C$_{28}$H$_{31}$NO$_4$×1.8 H$_2$O (477.99): C 70.63, H 7.30, N 2.93; C 70.33, H 7.00, N 2.84.

PHARMACEUTICAL PREPARATIONS

For the preparation of a pharmaceutical formulation, the active ingredient may be formulated to an injection, capsule, tablet, suppository, solution or the like. Oral formulation and injection are preferably employed. The pharmaceutical formulation may comprise the δ-selective agonist alone or may also comprise expedients such as stabilizers, buffering agents, diluents, isotonic agents, antiseptics and the like. The pharmaceutical formulation may contain the above described active ingredient in an amount of 1–95% by weight, preferably 10–60% by weight. The dose of the active ingredient may appropriately be selected depending on the objects of administration, administration route and conditions of the patients. The active ingredient is administered in doses between 1 mg and 800 mg per day in case of administration by injection and in doses between 10 mg and 5 g per day in case of oral administration. The preferred dose for injection is 20–200 mg per day and the preferred amount for oral administration 50–800 mg per day.

BIOLOGICAL STUDIES

δ-Selective agonism was assessed using the electrical stimulated guinea-pig ileal longitudinal muscle preparations (GPI; containing m and k opioid receptors) (P. W. Schiller et al., Biochem. Biophys. Res. Commun., Vol. 58: 11–18, 1978; J. Di Maio et. al., J. Med. Chem., Vol. 25: 1432–1438, 1982) and mouse vas deferens preparation (MVD: containing μ, κ and δ opioid receptors). The activities of the compounds to inhibit the contraction of the organs were measured. In the GPI, compounds 1 and 12 did not show inhibition of contraction up to 5.000 nM and 10.000 nM, respectively. These findings suggest that there is no agonist effect at m and k opioid receptors. In MVD, the tested compounds showed δ-selective agonism.

The biological studies of the novel morphinane derivatives of the formula (I) of the present invention have thus shown that these compounds have selectivity for δ opioid receptors and are effective as opioid agonists. Studies with δ-selective opioid agonists have shown that this class of compounds does not have dependence liability and produces substantially less respiratory depression than morphine. Dependence liability and respiratory depression are the most serious side effects of the opioid agonists used as analgesics (e.g. morphine). Accordingly, compounds according to the present invention useful as analgesics without showing the most serious side effects of opioid analgesics.

I claim:
1. A compound having the chemical structure of formula (I)

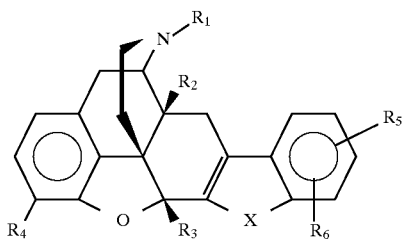

wherein:
- $R_1$ is selected from the group consisting of $C_1$–$C_6$ alkyl; and hydrogen;
- $R_2$ is selected from the group consisting of hydrogen; hydroxy; $C_1$–$C_6$ alkoxy; $C_7$–$C_{16}$ arylalkyloxy wherein the aryl is $C_6$–$C_{10}$ aryl and the alkyloxy is $C_1$–$C_6$ alkyloxy;
- $R_3$ is a linear $C_1$–$C_6$ alkyl;
- $R_4$ is selected from the group consisting of hydrogen; hydroxy; and $C_1$–$C_6$ alkoxy;
- $R_5$ and $R_6$ each and independently are selected from the group consisting of hydrogen; and $C_1$–$C_6$ alkyl; and
- X is $NR_9$ wherein $R_9$ is selected from the group consisting of H; and $C_1$–$C_6$ alkyl; and wherein any aryl group in said compound may be unsubstituted or mono-, di-, or tri-substituted independently with hydroxy; halo; nitro; cyano; thiocyanato; trifluoromethyl; $C_1$–$C_3$ alkyl; $C_1$–$C_3$ alkoxy; $CO_2H$; $CONH_2$; $CO_2(C_1$–$C_3$ alkyl); $CONH(C_1$–$C_3$ alkyl); $CON(C_1$–$C_3$ alkyl)$_2$; $CO(C_1$–$C_3$ alkyl); amino; ($C_1$–$C_3$ monoalkyl) amino; ($C_1$–$C_3$ dialkyl) amino; $C_5$–$C_6$ cycloalkylamino; ($C_1$–$C_3$ alkanoyl) amido; SH; $SO_3H$; $SO_3$($C_1$–$C_3$ alkyl); $SO_2(C_1$–$C_3$ alkyl); $SO(C_1$–$C_3$ alkyl); $C_1$–$C_3$ alkylthio; and $C_1$–$C_3$ alkanoylthio;

and the pharmacologically acceptable salts of the compounds of the formula (I).

2. The compound of claim 1 wherein:
- $R_1$ is selected from the group consisting of hydrogen; methyl; ethyl; n-propyl; and isopropyl;
- $R_2$ is selected from the group consisting of methoxy; ethoxy; and n-propyloxy;
- $R_3$ is selected from the group consisting of methyl; and ethyl;
- $R_4$ is selected from the group consisting of hydroxy; and methoxy;
- $R_5$ and $R_6$ are each hydrogen; and
- X is selected from the group consisting of NH; and $NCH_3$.

3. The compound of claim 1, wherein:
- $R_1$ is $CH_3$;
- $R_2$ is selected from the group consisting of methoxy; ethoxy; and n-propyloxy;
- $R_3$ is $CH_3$;
- $R_4$ is hydroxy;
- $R_5$ and $R_6$ are each hydrogen; and
- X is NH.

4. A compound selected from the group consisting of:
- 6,7-dehydro-4,5α-epoxy-14-ethoxy-3-hydroxy-5,17-dimethyl-6,7-2',3'-indolomorphinan;
- 6,7-dehydro-4,5α-epoxy-3,14-dimethoxy-5,17-dimethyl-6,7-2',3'-indolomorphinan;
- 6,7-dehydro-4,5α-epoxy-3-hydroxy-14-methoxy-5,17-dimethyl-6,7-2'3'-indolomorphinan;
- 6,7-dehydro-4,5α-epoxy-3,14-dihydroxy-5,17-dimethyl-6,7-2'3'-indolomorphinan x HBr;
- 7,8-dehydro-4,5α-epoxy-14-hydroxy-3-methoxy-5,17-dimethyl-6,7-2'3'-indolomorphinan x HBr;
- 6,7-dehydro-4,5α-epoxy-3-hydroxy-14-methoxy-5-methyl-6,7-2',3'-indolomorphinan;
- 6,7-dehydro-4,5α-epoxy-3-hydroxy-5,17-dimethyl-14-n-propyloxy-6,7-2',3'-indolomorphinan methane sulfonate;
- 6,7-dehydro-4,5α-epoxy-14-ethoxy-17-isopropyl-3-methoxy-5-methyl-6,7-2',3'-benzo[b]furanomorphinan.

5. The compound of claim 1, wherein said compound is in the form of a pharmaceutically acceptable salt.

6. The compound of claim 5, wherein said salt is an inorganic salt.

7. The compound of claim 5, wherein said salt is an organic salt.

8. A pharmaceutical composition comprising, in admixture with a pharmaceutically acceptable carrier, the compound of any one of claims 1–4 and 5–7 in an analgesically effective amount.

9. A method for the treatment of a subject suffering from pain, comprising administering to said subject the compound of any one of claims 1–4 and 5–7, wherein said compound is administered in an amount sufficient to reduce or eliminate said pain.

* * * * *